United States Patent [19]

Maryanoff

[11] Patent Number: 4,595,688
[45] Date of Patent: Jun. 17, 1986

[54] HEXAHYDROPYRROLO[2,1-a]ISOQUINO-LINE DERIVATIVES AND ANTIDEPRESSANT USE THEREOF

[75] Inventor: Bruce E. Maryanoff, New Hope, Pa.

[73] Assignee: McNeilab, Inc., Fort Washington, Pa.

[21] Appl. No.: 611,646

[22] Filed: May 18, 1984

Related U.S. Application Data

[63] Continuation-in-part of Ser. No. 507,250, Jun. 23, 1983, abandoned.

[51] Int. Cl.[4] .................... A61K 31/47; C07D 221/18; C07D 221/22; C07D 451/00
[52] U.S. Cl. .................................... 514/285; 546/71; 546/94; 514/294
[58] Field of Search .................... 546/94, 71; 514/294, 514/285

[56] References Cited

U.S. PATENT DOCUMENTS

| | | | |
|---|---|---|---|
| 3,383,388 | 5/1968 | Houlihan et al. | 546/94 |
| 3,502,679 | 3/1970 | Houlihan et al. | 546/71 |
| 3,635,984 | 1/1972 | Houlihan et al. | 546/71 |
| 3,892,752 | 7/1975 | Houlihan et al. | 546/71 |

FOREIGN PATENT DOCUMENTS

| | | | |
|---|---|---|---|
| 2081412 | 1/1971 | France | 546/71 |
| 1153670 | 5/1969 | United Kingdom | 546/71 |

OTHER PUBLICATIONS

"Use of the Butaclamol Template in a Search for Antipsychotic Agents with Lessened Side Effects", by Michael J. Kukla et al., in the Journal of Medicinal Chemistry, (1979) vol. 22 pp. 401–406.
Ronald C. Griffith et al., Journal of Medicinal Chemistry, vol. 27 pp. 995–1003 (Aug., 1984).
Abstract of European Pat. No. 107,825-A.
"Synthesis and Pharmacological Evaluation of Some Pyrrolo[2,1-a]Isoquinolines" Cesare Casagrande et al., Jul. 1968, pp. 765–770, vol. 11.
"Intramolecular Amidoalkylations at Carbon. Synthesis of Heterocyclic Amines", M. Winn et al., vol. 33, No. 10, Oct. 1968, pp. 3779–3783.

*Primary Examiner*—Henry R. Jiles
*Assistant Examiner*—Robert C. Whittenbaugh
*Attorney, Agent, or Firm*—David J. Levy

[57] ABSTRACT

Novel compounds are disclosed, which are derivatives of 1,2,3,5,6,10b-hexahydropyrrolo[2,1-a]-isoquinolines, represented by general formula (I):

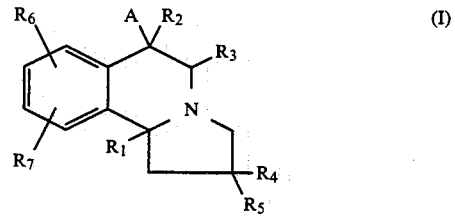

as well as pharmaceutical compositions and methods for the treatment of depression in warm-blooded animals, e.g., man. Novel intermediates are also part of the invention.

12 Claims, No Drawings

HEXAHYDROPYRROLO[2,1-A]ISOQUINOLINE DERIVATIVES AND ANTIDEPRESSANT USE THEREOF

The present application is a continuation-in-part of U.S. Ser. No. 507,250 filed June 23, 1983, now abandoned.

This invention relates to novel chemical compounds, which are derivatives of 1,2,3,5,6,10b-hexahydropyrrolo[2,1-a]isoquinolines, and nontoxic, pharmaceutically-acceptable salts thereof. It also relates to novel synthetic intermediates and processes leading to said compounds. Compounds and pharmaceutically-acceptable acid addition salts thereof, of the invention are of free base form of the general formula (I):

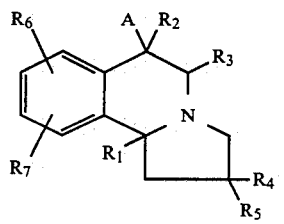

wherein
$R_1$ is hydrogen or lower alkyl having one to four carbons;
$R_2$ is hydrogen, lower alkyl having one to four carbons, fluoro, hydroxy, or lower alkoxy having one to four carbons;
$R_3$ is hydrogen, methyl or phenyl;
$R_4$ and $R_5$ are the same and both are hydrogen, or different and each is selected from the group of hydrogen or lower alkyl having one to four carbons;
$R_6$ and $R_7$ are the same or different and each is selected from the group hydrogen, lower alkyl having one to four carbons, lower alkoxy having one to four carbons, hydroxy, or halogen, or else are taken together as methylenedioxy; and
A is selected from the group of units of the following formulas (1), (2), or (3),

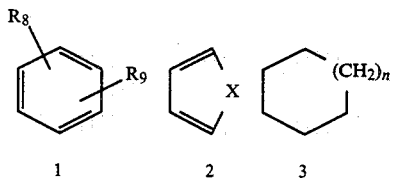

wherein in the benzene unit of formula (1), $R_8$ and $R_9$ are selected from the group hydrogen, lower alkyl having one to six carbons, perfluoro(lower)alkyl having one to four carbons, hydroxy, lower alkoxy having one to four carbons, carb(lower)alkoxy having one to five carbons, lower acylamino (one to five carbons), benzoylamino($C_6H_5CONH$—), cyano, carboxamido($H_2NCO$—), lower acyl of one to five carbons, lower alkylthio having one to four carbons, lower alkylsulfonyl having one to four carbons, nitro, amino, loweralkyl- or di(lower)alkyl-amino having one to four carbons in each alkyl, or halogen; wherein in the heteroaromatic unit of formula (2), X is oxygen or sulfur; and wherein in the cycloalkyl unit of formula (3), n=0, 1 or 2.

Formulas (1), (2) and (3) may be attached at any carbon atom vertex thereof.

As used herein, the terms "lower alkyl", "lower alkoxy", "lower alkylthio", "lower alkylsulfonyl", and "perfluoro(lower)alkyl" refer to straight- or branched-chain carbon skeletons, within the carbon-atom limits defined. The term halo (or halogen) is generic for fluorine, chlorine, bromine, and iodine.

Each formula (I) compound describes and comprises diastereomeric substances, themselves pairs of enantiomers. The diastereomers, isolated in their pure form, may differ in biological activity. The compounds of formula (I) constitute valuable therapeutic agents by their possession of psychotropic activity, particularly antidepressant activity.

The various diastereomers of each formula (I) compound are distinguished herein using the nomenclature recommended by Chemical Abstracts for representing the relative configuration of diastereomers of fused-ring compounds ($\alpha/\beta$ nomenclature). This requires that the stereocenter corresponding to the lowest numbered atom in the ring system (numbered according to convention) be designated $\alpha$ and that the remaining stereocenters be labeled $\alpha$ or $\beta$ relative to the first-assigned center. For example:

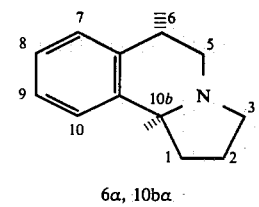

6α, 10bα

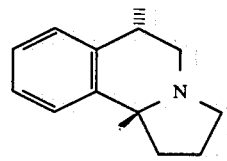

6α, 10bβ

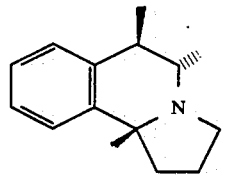

5α, 6β, 10bβ

The new compounds of the present invention can be prepared by various methodologies, known to those skilled in the art of organic chemistry. Some examples of important synthetic routes are illustrated below; these are exemplary methods and should not be taken as exhaustive. For the sake of simplicity, the routes are depicted without substituents on the aliphatic chains or aromatic rings, but this should not be construed to limit necessarily the scope of the synthetic process.

The $R_1$, $R_2$, $R_3$, $R_4$, $R_5$, $R_6$ and $R_7$ groups of formula (I) are depicted in the following routes as a specific moieties, e.g., hydrogen or methyl, for the purpose of specific exemplification. However the other $R_1$-$R_7$ possible moieties may be used in their place by choice of a different starting material. For example, substitution of di-(para-tolyl)ethylamine for diphenylethylamine as (II) in Route (A) will result in formula (I) with $R_6$ as 9-methyl and A as para-tolyl.
(A) Keto-Acid, Acyliminium-Ion Route:
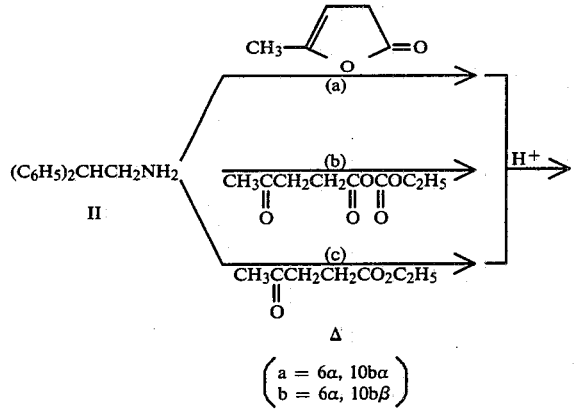
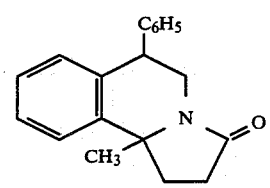
III
[H] ↓
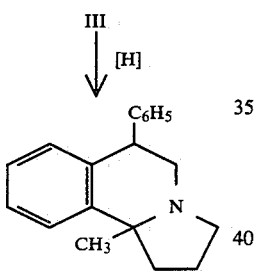
IV
(B) Imide, Acyiminium-Ion Route:
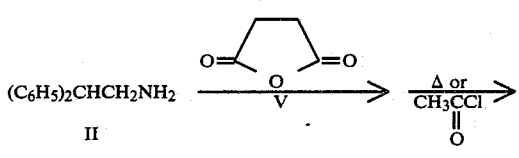
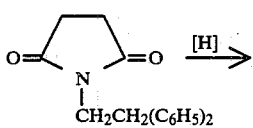
VI
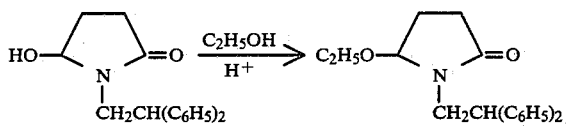
VII    VIII
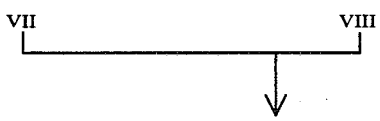
-continued
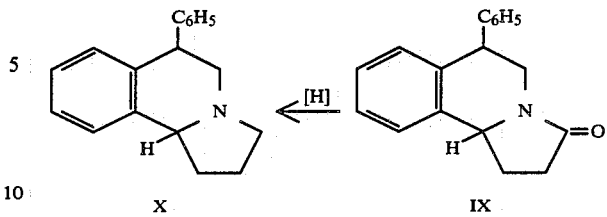
X           IX
(C) Mandelic-Acid Route:
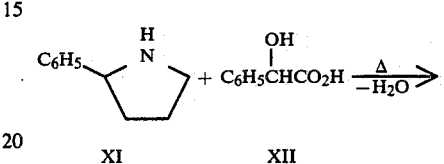
XI           XII
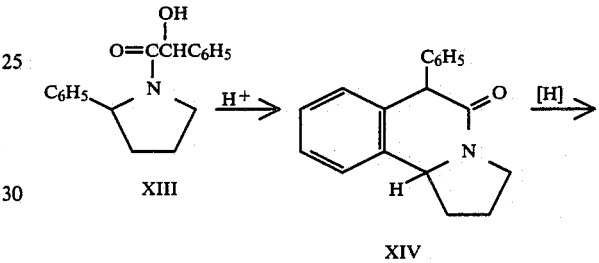
XIII           XIV
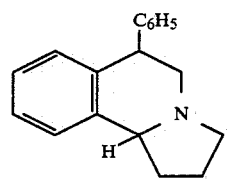
X
(D) Styrene-Oxide Route:
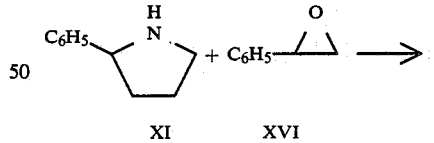
XI           XVI
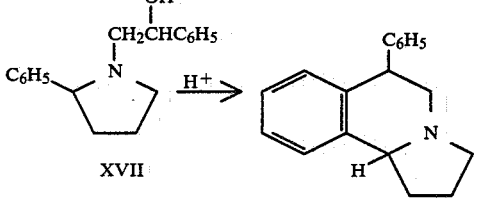
XVII           X
(E) Butyrolactone Route:

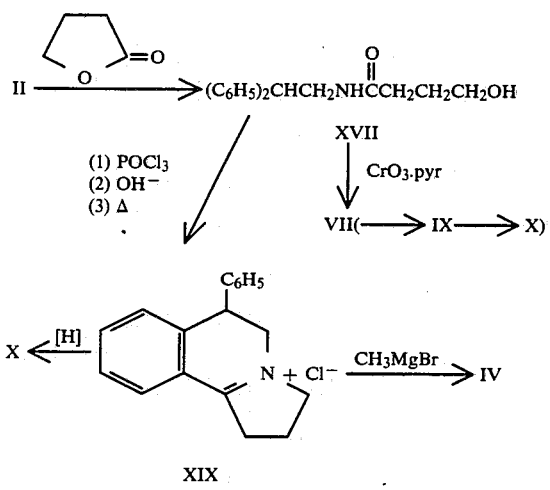

The keto-acid route (A) entails condensation of an arylethylamine, such as II, with (a) α-angelicalactone (or congeners thereof) in an inert solvent, such as methylene chloride or ethyl acetate, around ambient temperature, or (b) the mixed carbonic anhydride of levulinic acid (or congeners thereof) in an inert solvent, such as tetrahydrofuran, ethyl ether or toluene, around 0° C., or (c) a simple ester of levulinic acid (or congeners thereof) without solvent at elevated temperatures around 175°–225° C. The adduct (not shown) is then cyclized with an acid catalyst to a lactam intermediate, such as III. The acid catalyst must be strong when cyclization is to take place on an aromatic ring not bearing a good electron-donating substituent (e.g., methoxy) ortho or para to the site of ring closure: e.g., polyphosphoric acid, liquid hydrogen fluoride, pyridinium polyhydrogen fluoride, or trifluoromethanesulfonic acid. When an electron-donating group is present in a proper orientation, cyclization can be effected with weaker acid catalysts, e.g., ethanolic hydrogen chloride or trifluoroacetic acid, and cyclization will preferentially occur on the ring having the greater activation in a competitive situation. The final product, such as IV, is then obtained by reduction of the amide functionality, employing aluminum or boron hydrides, e.g., lithium aluminum hydride or borane-tetrahydrofuran.

The imide route (B) is analogous to the keto-acid route, but yields 10b-unsubstituted derivatives. This route involves reaction of an arylethylamine, such as II, with succinic anhydride V (or congeners thereof) in an inert solvent, such as methylene chloride, ethyl acetate, or tetrahydrofuran, around ambient temperature. The amide-acid intermediate (not shown) is converted to a succinimide, such as VI, by heating without solvent at 150°–200° C., or by addition of acetylchloride to the original mixture and heating at 40°–70° C. The succinimide is then reduced with sodium borohydride in ethanol, as described by Speckamp (J. C. Hubert, et al., Tetrahedron, 31, 1437 (1975)), or by diisobutylaluminum hydride, as described by Hart (D. J. Hart and K. Kanai, J. Org. Chem., 47, 1555 (1982)). One may employ either a hydroxy or ethoxy species, such as VII or VIII, in an acid-catalyzed cyclization as described above for the keto-acid route, affording a lactam such as IX. The lactam is then reduced to a target amine, such as X, as described above for the keto-acid route.

The mandelic-acid route (C) entails thermal condensation (140°–170° C.) of a 2-arylpyrrolidine, such as XI, with a mandelic acid, such as XII, with continuous removal of water, to give a mandelamide, such as XIII. The mandelamide is cyclized to a lactam, such as XIV, with a strong acid catalyst, e.g., polyphosphoric acid, sulfuric acid, or liquid hydrogen fluoride. The lactam is reduced preferably with a Lewis acid-type hydride reagent such as with borane-tetrahydrofuran to yield a target amine such as X.

The styrene-oxide route (D) involves condensation of a 2-arylpyrrolidine, such as XI, with a styrene oxide, such as XVI, in refluxing ethanol or in sulfolane at 140°–170° C., to give an amino alcohol, such as XVII. The amino alcohol is cyclized by heating with an acid catalyst, e.g., polyphosphoric acid, 48% hydrobromic acid, or sulfuric acid, to furnish a product amine, such as X.

The butyrolactone route (E) is based on reaction of an arylethylamine, such as II, with butyrolactone (or congeners thereof), without solvent around 100° C., to give an amido alcohol, such as XVIII. The amido alcohol can be converted to a key intermediate of the imide route, such as VII, for transformation into target compounds of formula (I), as indicated in route (B), by careful oxidation with chromium trioxide in pyridine. Alternatively, the amido alcohol can be converted to an iminium salt, such as XIX, with phosphorus oxychloride in toluene at 110° C., followed by treatment of the toluene-insoluble material with aqueous sodium hydroxide and heating in toluene solution. The iminium salt can be reduced to a target amine, such as X, with NaBH$_4$ or LiAlH$_4$. The iminium salt can also be reacted with an organometallic reagent, such as an organolithium or organomagnesium (Grignard) compound to afford 10b-substituted target amines of formula (I). For example, a Grignard reaction with methyl magnesium bromide, in ether or tetrahydrofuran, leads to a 10b-methyl compound of formula (I), such as IV.

The cyclization reactions in routes (A)–(E) afford mixtures of diastereomers. In certain instances, product mixtures may be highly enriched in specific diastereomers. The diastereomers may be separated and purified by standard techniques known to those skilled in the art of organic chemistry, such as fractional crystallization or liquid chromatography of free bases, or fractional crystallization of acid-addition salts.

Diastereomers may be interconverted by base-induced exchange of protons at the 6 and/or 10b positions. Specifically, heating of lactam diastereomers related to formula (I) compounds possessing 6 and/or 10b protons in aqueous dimethylsulfoxide around 100°–150° C. in the presence of an alkali metal carbonate, such as K$_2$CO$_3$, for 1–1000 hours can give rise to equilibrium mixtures of diastereomers. Also, heating of amine diastereomers of formula (I) possessing 6 and/or 10b protons in aqueous dimethylsulfoxide around 80°–150° C. in the presence of an alkali metal hydroxide such as NaOH, for 1–60 hours, can give rise to equilibrium mixtures of diastereomers. Such equilibration tactics can enhance the proportions of minor diastereomers in comparison to the original product mixtures from cyclization. In appropriate instances, the equilibration method can alter relative configuration between the 6 stereocenter in relation to the 2, 5, and 10b stereocenters for compounds of general formula (I) bearing a 6-position proton, between the 10b stereocenter and the 2, 5, and 6 stereocenters for compounds of formula (I) bearing a 10b-position proton, but not between the 2 and 5 stereocenters in compounds of formula (I).

Another means of changing the original diastereomeric composition of formula (I) compounds bearing a 10b-position proton involves oxidation with mercuric acetate, followed by direct reduction of the intermediate iminium salt, such as XVIII, with NaBH$_4$, LiAlH$_4$, or catalytic hydrogenation, see route (E). Also, the iminium salt can be isomerized to an enamine such as XXI and reduced by catalytic hydrogenation over platinum oxide.

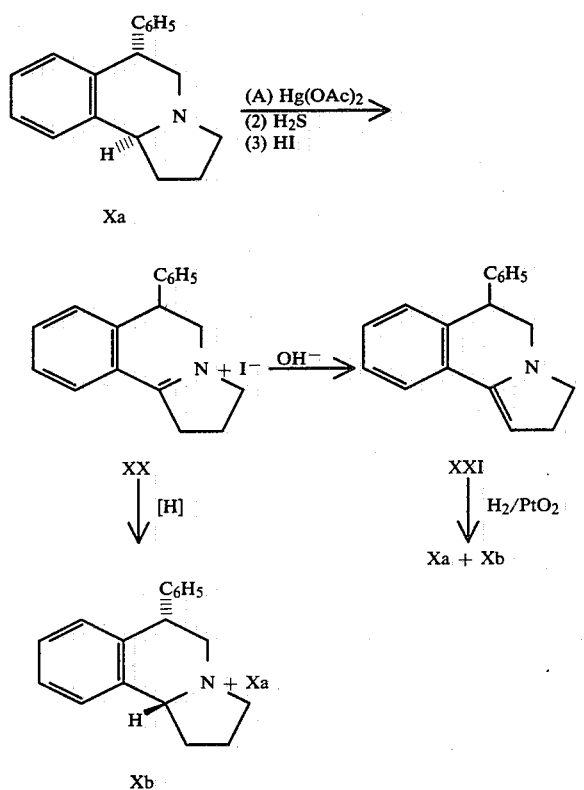

The compounds of this invention can be prepared and utilized in the form of the free base. The compounds can also be used as pharmaceutically-acceptable, nontoxic addition salts of inorganic or organic acids such as halogen acids, e.g., HCl, HBr, HI sulfuric acid, maleic acid, hexamic acid, perchloric acid, fumaric acid, saccharin, and the like.

Compounds of formula (I) wherein A is hydroxyphenyl were generally prepared from the corresponding methoxy derivatives by standard demethylation using 48% HBr in acetic acid at 100°-130° C. or BBr$_3$ in methylene chloride at −78° to −20° C. Compounds of formula (I) wherein A is aminophenyl were obtained from nitrophenyl congeners by reduction of the nitro compound with hydrogen in the presence of a catalyst, such as PtO$_2$, in ethanol. From the aminophenyl derivative, the compound wherein R$_8$ or R$_9$ is loweracylamino or benzoylamino may be prepared by reaction with the desired alkanoyl chloride or benzoyl chloride, respectively as described in the Examples. The acylamino derivative may be reduced with BH$_3$ to yield a compound wherein R$_8$ or R$_9$ is alkylamino, e.g., by reducing the compound wherein A is acetylamino (CH$_3$CONH—) substituted phenyl to one wherein A is ethylaminophenyl. The compounds of the invention wherein A is phenyl substituted by cyano may be obtained by reaction of the corresponding bromo compound with cuprous cyanide with tetrakistriphenylphosphine palladium and from such a cyano product, the corresponding carboxamide, e.g., R$_8$=—CONH$_2$ may be obtained by reaction with a strong base such as potassium hydroxide. When R$_4$ and/or R$_5$ of formula (I) are alkyl, the corresponding hydrogen substituted compounds may be prepared and then alkylated by reaction with lithium diisopropylamide in tetrahydrofuran with the appropriate alkyl iodide.

The formula (I) compounds are endowed with useful biological activity in the central nervous system. More particularly, the formula (I) compounds exhibit antidepressant activity in warm-blooded animals. In the group of formula (I) compounds, useful antidepressant activity may be associated with particular diastereomers.

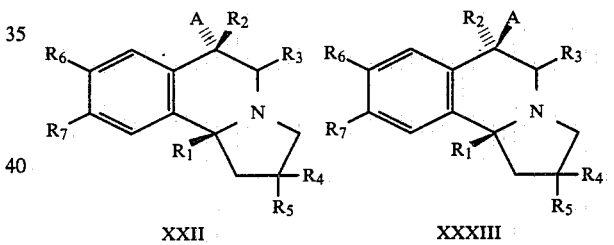

The utility of the novel compounds of this patent is based on a standard test for antidepressant agents involving antagonism of the depressant effects of tetrabenazine (TBZ). This is the "classical" tetrabenazine antagonism assay described in U.S. Pat. No. 3,787,577. In this test, mice are injected with a test compound 30 minutes prior to the injection of 32 mg/kg i.p. of TBZ, a drug which decreases normal exploratory activity and induces ptosis. After 30 minutes, the mice are tested for two parameters: the presence of normal exploratory activity (EA) and reversal of ptosis (Pt). A control group of mice is given only 32 mg/kg i.p. of TBZ. The biological activity of the novel compounds of this invention may be understood by some representative, nonlimiting examples, presented in Tables I and II.

Tables I lists the compounds tested by a compound number, structural formula, HX or acid addition salt form in which the compound was tested, test data, and internal code number (McN No.). Table II names the various Table I compounds.

TABLE 1++

| No. | Compound | HX | TBZ ED₅₀* EA/Pt (i.p.) | McN No. (m.p.; solv.)+ |
|---|---|---|---|---|
| IVb | | hexamic acid | 9.2/3.8 | 4803 (136–38; P/EE) |
| Xb | | fumaric acid | 0.34/0.07 | 4612-Z (170–72; E) |
| XXIV | | fumaric acid | CA. 40/8.0 | 5531 (199–205 d; E/W) |
| XXV | | HBr | 27/0.7 | 4985 (261–65; M/P) |
| XXVI | | HBr | 0.87/0.33 | 5175 (255–57; M) |
| XXVII | | fumaric acid | 17/7.2 | 5199 (129–32; M/P) |

TABLE 1++-continued

| No. | Compound | HX | TBZ ED$_{50}$*<br>EA/Pt (i.p.) | McN No.<br>(m.p.; solv.)+ |
|---|---|---|---|---|
| XXVIII | (cyclohexyl-substituted pyrrolo-isoquinoline) | HBr | 6.4/1.9 | 5254<br>(169–72; M/EA) |
| XXIX | (4-chlorophenyl-substituted pyrrolo-isoquinoline) | HBr | 0.27/0.13 | 5292<br>(290–93; M) |
| XXX | (4-chlorophenyl-substituted pyrrolo-isoquinoline, alt. stereochem.) | fumaric acid | 8.1/5.4 | 5321<br>(179–81; M/P) |
| XXXI | (4-methoxyphenyl-substituted pyrrolo-isoquinoline) | HBr | ca. 60/3.0 | 5344<br>(202–204; M/P) |
| XXXII | (4-chlorophenyl, chloro-substituted pyrrolo-isoquinoline) | HClO$_4$ | 37/4.0 | 4914<br>(244–46 d; M) |

TABLE 1++-continued

| No. | Compound | HX | TBZ ED$_{50}$* EA/Pt (i.p.) | McN No. (m.p.; solv.)+ |
|---|---|---|---|---|
| XXXIII | (4-methoxyphenyl isoquinoline-pyrrolidine structure) | HBr | 7.0/0.19 | 5346 (241–44; M/P) |
| XXXIV | (phenyl, OH isoquinoline-pyrrolidine structure) | fumaric acid | 8.4/1.6 | 5335 (178–81; E) |
| XXXV | (3,4-dihydroxyphenyl isoquinoline-pyrrolidine structure) | HBr | 1.4/0.13 | 5375 (244–48 d; B) |
| XXXVI | (4-hydroxyphenyl isoquinoline-pyrrolidine structure) | HBr | ca. 14/10 | 5394 (257–60; M/P) |
| XXXVII | (3,4-dihydroxyphenyl isoquinoline-pyrrolidine structure) | HBr | 30/1.8 | 5416 (246–48 d; M/B) |

TABLE 1++-continued

| No. | Compound | HX | TBZ ED$_{50}$*<br>EA/Pt (i.p.) | McN No.<br>(m.p.; solv.)+ |
|---|---|---|---|---|
| XXXVIII | 4-NO$_2$-phenyl isoquinoline-pyrrolidine | HBr | 0.51/0.15 | 5462<br>(277–29 d; E/W) |
| XXXIX | 7-methoxy, 4-phenyl isoquinoline-pyrrolidine | HBr | ca. 40/8 | 5480<br>(209–12; E/W) |
| XL | 3-OCH$_3$-phenyl isoquinoline-pyrrolidine | fumaric acid | ca. 0.17/<br>ca. 0.07 | 5494<br>(185–91; P) |
| XLI | 3-OH-phenyl isoquinoline-pyrrolidine | HBr | >10/0.11 | 5497<br>(244–46; P) |
| XLII | 4-Cl-phenyl, 7-Cl isoquinoline-pyrrolidine | tosic acid | 100/37 | 4721<br>(182–84; M/EE) |
| XLIII | 4-phenyl-4-OH isoquinoline-pyrrolidine | HBr | 33/5.0 | 5386<br>(211–12; M/P) |

TABLE 1++-continued

| No. | Compound | HX | TBZ ED$_{50}$* EA/Pt (i.p.) | McN No. (m.p.; solv.)+ |
|---|---|---|---|---|
| XLIV | (3-hydroxyphenyl pyrrolo-isoquinoline) | HBr | 37% @ 30/ 3.1 | 5498 (252-53; E/EE) |
| XLV | (3,4-dimethoxyphenyl pyrrolo-isoquinoline) | HBr | 33% @ 30/ 0.14 | 5426 (235-37 d; A) |
| XLVI | (phenyl, methyl pyrrolo-isoquinoline) | HBr | 22.5/16 | 4981 (219-26; M/P/EE) |
| XLVII | (phenyl, 8-methoxy pyrrolo-isoquinoline) | None | 2.8/ca. 6.5 | 5605 (151-52; E) |
| XLVIII | (4-aminophenyl pyrrolo-isoquinoline) | HBr | 1.4/0.41 | 5556 (220-245 d; M/P) |

TABLE 1++-continued

| No. | Compound | HX | TBZ ED$_{50}$*  EA/Pt (i.p.) | McN No. (m.p.; solv.)+ |
|---|---|---|---|---|
| XLIX | (3-CF$_3$-phenyl isoquinoline-pyrrolidine structure) | HCl | 1.2/0.43 | 5558 (180–83 d; D/E) |
| L | (4-F-phenyl, 8-F, 10b-CH$_3$ isoquinoline-pyrrolidine structure) | HBr | 6.1/5.6 | 5687 (244–46; P) |
| LI | (2-Cl-phenyl isoquinoline-pyrrolidine structure) | HBr | 37% @ 60/ 0.20 | 5707 (213–220; M/P) |
| LII | (3-phenyl isoquinoline-pyrrolidine structure) | HBr | Ca. 30/32 | 5250 (230–2325; E) |
| LIII | (phenyl, F substituted isoquinoline-pyrrolidine structure) | HCl | 60% @ 40/1.2 | 5603 (192–193; P) |

*ED$_{50}$ given in mg/kg for each parameter (except for percent inhibition at a certain dose in mg/kg, given for four examples: XLIV, XLV, LI and LIII).
+m.p. of the acid-solution salt in °C. (d = decomposition); recrystallization solvent (E = absolute ethanol; M = methanol, P = 2-propanol; EE = ethyl ether; EA = ethyl acetate; B = t-butanol; W = water; A = acetonitrile; Ac = acetone; D = dichloromethane; T = tetrahydrofuran).
++Structure assignments are based mainly on $^1$H NMR spectral data. X-ray crystallographic analyses were performed on XXV, XLVI, the lactam precursor to XXVIII, and the lactam precursor to Xa (i.e., IXa) to establish stereochemistry for the entire series.

TABLE II

| No. | McN No. | Name of compound |
|---|---|---|
| IVb | 5803 | [6α,10bβ]-1,2,3,5,6,10b-Hexahydro-10b-methyl-6-phenylpyrrolo[2,1-a]isoquinoline |
| Xb | 4612-Z | [6α,10bβ]-1,2,3,5,6,10b-Hexahydro-6-phenyl-pyrrolo[2,1-a]isoquinoline |
| XXIV | 5531 | 6α-(3,4-Dichlorophenyl)-1,2,3,5,6,10bα-hexahydro- |

TABLE II-continued

| No. | McN No. | Name of compound |
|---|---|---|
| XXV | 4985 | pyrrolo[2,1-a]isoquinoline 1,2,3,5,6,10bβ-Hexahydro-6-methyl-6α-phenylpyrrolo[2,1-a]isoquinoline |
| XXVI | 5175 | [6α,10bβ]-1,2,3,5,6,10b-Hexahydro-8,9-dihydroxy-6-phenylpyrrolo[2,1-a]isoquinoline |
| XXVII | 5199 | [6α,10bβ]-1,2,3,5,6,10b-Hexahydro-8,9-dimethoxy-6-phenylpyrrolo[2,1-a]isoquinoline |
| XXVIII | 5254 | [6α,10β]-6-Cyclohexyl-1,2,3,5,6,10b-hexahydropyrrolo[2,1-a]isoquinoline |
| XXIX | 5292 | [6α,10bβ]-6-(4-Chlorophenyl)-1,2,3,5,6,10b-hexahydropyrrolo[2,1-a]isoquinoline |
| XXX | 5321 | 6α-(4-Chlorophenyl)-1,2,3,5,6,10bα-hexahydropyrrolo[2,1-a]isoquinoline |
| XXXI | 5344 | 1,2,3,5,6,10bα-Hexahydro-6α-(4-methoxyphenyl)pyrrolo[2,1-a]isoquinoline |
| XXXII | 4914 | [6α,10bβ]-9-Chloro-6-(4-chlorophenyl)-1,2,3,5,6,10b-hexahydropyrrolo[2,1-a]isoquinoline |
| XXXIII | 5346 | 1,2,3,5,6,10bβ-Hexahydro-6α-(4-methoxyphenyl)pyrrolo[2,1-a]isoquinoline |
| XXXIV | 5335 | 1,2,3,5,6,10b-Hexahydro-6-phenylpyrrolo[2,1-a]isoquinolin-6-ol |
| XXXV | 5375 | 4-(1,2,3,5,6,10bβ-Hexahydropyrrolo[2,1-a]isoguinolin-6α-yl)benzene-1,2-diol |
| XXXVI | 5397 | 4-(1,2,3,5,6,10bα-Hexahydropyrrolo[2,1-a]isoquinolin-6α-yl)phenol |
| XXXVII | 5416 | 4-(1,2,3,5,6,10bα-Hexahydropyrrolo[2,1-a]isoquinolin-6a-yl)-1,2-benzenediol |
| XXXVIII | 5462 | 1,2,3,5,6,10bβ-hexahydro-6α-(4-nitrophenyl)-pyrrolo[2,1-a]isoquinoline |
| XXXIX | 5480 | 1,2,3,5,6,10bα-Hexahydro-9-methoxy-6α-phenylpyrrolo[2,1-a]isoquionline |
| XL | 5494 | 1,2,3,5,6,10bβ-Hexahydro-6α-(3-methoxyphenyl)pyrrolo[2,1-a]isoquinoline |
| XLI | 5497 | 3-(1,2,3,5,6,10bβ-Hexahydropyrrolo[2,1-a]isoquinolin-6α-yl)phenol |
| XLII | 4721 | [6α,10bα]-9-Chloro-6-(4-chlorophenyl)-1,2,3,5,6,10b-hexahydropyrrolo[2,1-a]isoquinoline |
| XLIII | 5386 | 1,2,3,5,6,10b-Hexahydro-6-phenylpyrrolo[2,1-a]isoquinolin-6-ol |
| XLIV | 5498 | 3-(1,2,3,5,6,10bα-Hexahydropyrrolo[2,1-a]isoquinolin-6α-yl)phenol |
| XLV | 5426 | 1,2,3,5,6,10bβ-Hexahydro-6α-(3,4-dimethoxyphenyl)pyrrolo[2,1-a]isoquinoline |
| XLVI | 4981 | 1,2,3,5,6,10bα-Hexahydro-6-methyl-6α-phenylpyrrolo[2,1-a]isoquinoline |
| XLVII | 56.5 | 1,2,3,5,6,10bβ-Hexahydro-7-methoxy-6α-phenylpyrrolo[2,1-a]isoquinoline |
| XLVIII | 5556 | 4-(1,2,3,5,6,10bα-Hexahydropyrrolo[2,1-a]isoquinoline-6α-yl)benzenamine |
| XLIX | 5558 | 1,2,3,5,6,10bβ-Hexahydro-6α-[(3-trifluoromethyl)phenyl]-pyrrolo[2,1-a]isoquinoline |
| L | 5687 | 9-Fluoro-6α-(4-fluorophenyl)-1,2,3,5,6,10b-hexahydro-10bβ-methylpyrrolo[2,1-a]isoquinoline |
| LI | 5707 | [6α,10bβ]-6-(2-chlorophenyl)-1,2,3,5,6,10b-hexahydropyrrolo[2,1-a]isoquinoline |
| LII | 5250 | 1,2,3,5,6,10bα-Hexahydro-5α-phenylpyrrolo[2,1-a]isoquinoline |
| LIII | 5603 | 6α-Fluoro-1,2,3,5,6,10bα-hexahydro-6-phenylpyrrolo[2,1-a]isoquinoline |

Other specific compounds which may be produced include the following:

LIV   1,2,3,5,6,10bα-hexahydro-6α-(4-nitrophenyl)-pyrrolo[2,1-a]isoquinoline;

LV   [6α,10bβ]-6-(4-bromophenyl)-1,2,3,5,6,10b-hexahydropyrrolo[2,1-a]isoquinoline; and LVI   1,2,3,5,6,10bβ-hexahydro-6α-(4-methylthiophenyl)pyrrolo[2,1-a]isoquinoline.

The compound designated LVI was produced through Route (C) and isolated by crystallization in methanol/ethanol as the perchlorate, mp=202°-203.5° C. Preferred compounds of the invention include those designated XLIX, LI and LVI. In general, the 10bβ compounds show greater activity than the corresponding 10bα compounds.

The invention will be further understood by referring to the following examples, which illustrate the preparation of compounds according to the invention. These examples are given for the purpose of illustration and are not to be construed as limiting the invention in spirit or scope.

The following formulae (4), (5) and (6) are described hereinafter in Examples 1 and 2.

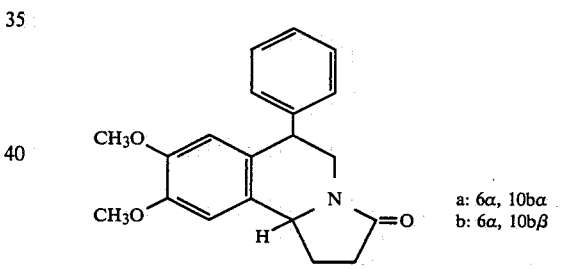

4 a: 6α, 10bα
b: 6α, 10bβ

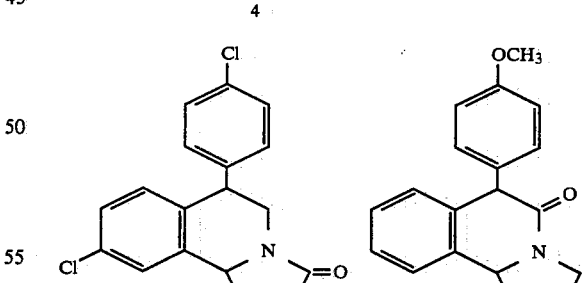

5                                6

EXAMPLE 1

Intermediate Lactams

The following procedures for the (A) route refer to the subroutes (a), (b) and (c) shown above.

General Procedure A/(a).

The enelactone (0.11 mol) shown in the scheme, e.g., α-angelica-lactone, in 30 ml of methylene chloride is combined with the arylethylamine, e.g., diphenylethylamine as shown in Route (A), above, (0.10 mol) in 30 ml of methylene chloride and let stand for 30 minutes. The solution is evaporated in vacuo to an oil, which is combined with PPA (200 g) and heated on a steam bath for four hours. The reaction mixture is poured into water and extracted with methylene chloride. The organic phase is washed once with water, once with saturated NaCl, and dried (MgSO$_4$). Evaporation in vacuo gives the lactam.

EXAMPLE A(a)

1,5,6,10b-Tetrahydro-10bα-methyl-6α-phenylpyrrolo[2,1-a]isoquinoline-3(2H)-one (IIIa)

2,2-Diphenylethylamine (6.0 g, 0.03 mol) and α-angelicalactone (3.24 g, 0.033 mol) were combined according to the general procedure. Work-up gave a mixture (94/6, GLC) of diastereomeric lactams IIIa and IIIb. Recrystallization from ethyl acetate/petroleum ether gave white crystalline IIIa, m.p. 135°–136° C.
General Procedure A/(b).

Ketoacid (0.10 mol) and dry triethylamine (10.2 g, 0.10 mol) are combined in 50 ml of methylene chloride and cooled to 0° C. Ethyl chloroformate (11.3 g, 0.10 mol) in 25 ml of methylene chloride is added slowly at 0° to 5° C., stirred at 0° C. for two hours and then at 10° C. for one hour. 2-Arylethylamine (0.10 mol) in 50 ml of methylene chloride is added to the mixture at 5° C. and the solution is stirred overnight at ambient temperature. Water (50 ml) is added and the reaction is stirred for two hours. The organic phase is separated and washed once with 5% HCl, once with 5% Na$_2$CO$_3$, and dried (Na$_2$SO$_4$). The solution is filtered and evaporated in vacuo to give the crude keto amide. To this crude material is added PPA (ca. 100 g) and the mixture is stirred on a steam bath for 20 hours. The mixture is poured into water and extracted with chloroform. The organic layer is washed once with H$_2$O, once with 5% Na$_2$CO$_3$, and dried (CaCl$_2$). Evaporation in vacuo gives crude lactam.

EXAMPLE A/(b)

1,5,6,10b-Tetrahydro-10bα-methyl-6α-phenylpyrrolo[2,1-a]isoquinoline-3(2H)-one (IIIa)

Following the above procedure, levulinic acid (11.8 g, 0.10 mol) was reacted with 2,2-diphenylethylamine (19.7 g, 0.10 mol) to give a mixture (16/1, GLC) of crude lactams IIIa and IIIb. The mixture was recrystallized from ethyl acetate/hexane to afford white crystalline IIIa, m.p. 177.5°–179° C.
General Procedure A/(c).

The keto ester (0.10 mol) and arylethylamine (0.10 mol) are combined and heated at 130° C. to 180° C. for 24 hours. The oil is placed under vacuum to remove any residual water or ethanol. This residue is combined with PPA (200 ml) and heated on a steam bath for 24 hours. Water (750 ml) is added and solid lactam is filtered or extracted.

EXAMPLE A/(c)

1,5,6,10b-Tetrahydro-10bα-methyl-6α-phenylpyrrolo[2,1-a]isoquinoline-3(2H)-one (IIIa)

2,2-Diphenylethylamine (19.7 g, 0.1 mol) and ethyl levelunate (14.6 g, 0.10 mol) was reacted according to the general procedure to give the lactams mixture IIIa and IIIb (ca. 15/1).

General Procedure B.

The arylethylamine (0.10 mol) in 100 ml of dry THF is added slowly to succinic anhydride (0.105 mol) in 100 ml of dry THF at 0° C. (Methylene chloride was also used). The reaction is stirred at ambient temperature for one hour and then evaporated in vacuo to the amide-acid. Cyclization of the amide-acid to the amide is accomplished by either (a) heating it without solvent at 170° C. for four hours or (b) combining it with 25 ml of acetyl chloride (AcCl) in 100 ml of ethyl acetate and heating the solution at reflux for ten hours. The imide may be recrystallized before use. The resulting imide is mixed with 400 ml of absolute ethanol, cooled to −10° C. with an ice/methanol bath, and stirred efficiently. NaBH$_4$ (0.40 mol) is added followed by 15 drops of CH$_3$SO$_3$H. The temperature is maintained at −10° C. to 0° C. with efficient stirring, and five drops of 2N ethanolic CH$_3$SO$_3$H are added every 15 minutes. After five hours, the 2N CH$_3$SO$_3$H is added more rapidly maintaining the temperature at 0° C. until the pH is less than three. During this addition, 200 ml of ethanol is added to thin out the foamy reaction solution. The reaction is then stirred for 16 hours at ambient temperature. The reaction is treated with water and methylene chloride. The organic solution is separated, washed once with water, once with saturated NaCl, and dried (MgSO$_4$). Evaporation in vacuo gives the ethoxypyrrolidinone. This ester is combined with PPA (100 ml) and heated on a steam bath for six hours (refluxing ethanolic HCl may be used instead of PPA when cyclizing onto electron rich aromatic groups). The reaction is poured into water and extracted with methylene chloride. The organic layer is separated, and washed once with water, once with saturated NaCl, dried (MgSO$_4$), and evaporated in vacuo to give the crude lactam.

EXAMPLE B1

1,5,6,10bα-Tetrahydro-6α-phenylpyrrolo-[2,1-a]isoquinoline-3(2H)-one (IXa)

Following the general procedure, 2,2-diphenylethylamine (19.7 g, 0.10 mol) and succinic anhydride (10.6 g, 0.105 mol, 99% assay) were combined and heated at 175° C. to give the imide. After reduction and cyclization with PPA, work-up gave white solid lactams IXa and IXb (93/7, GLC). Recrystallization from ethyl acetate/methanol furnished white crystalline IXa, m.p. 204.5°–205.5° C.

EXAMPLE B2

1,5,6,10bα-Tetrahydro-8,9-dimethoxy-6α-phenylpyrrolo[2,1-a]-isoquinoline-3(2H)-one (4a)

According to the general procedure, 2-(3,4-dimethoxyphenyl)-2-phenethylamine (35 g, 0.1 mol) and succinic anhydride (14.3 g, 0.143 mol) were combined and heated at 175° C. The crude imide was recrystallized from methanol to give purified imide. Imide material (15.0 g, 0.4 mol) was reduced the usual way to give the ethoxypyrrolidinone, which was dissolved in 100 ml of ethanol. Twenty drops of ethereal HCl was added and the reaction was heated at reflux. Even ten minutes, over the next 30 minutes, 1 ml of ethereal HCl was added to the reaction solution. The reaction was evaporated in vacuo to give an oily mixture (9/1, GLC) of lactams 4a and 4b. The mixture was recrystallized from ethyl acetate to afford white crystalline lactam 4a, m.p. 140°–141° C.
General Procedure C.

The mandelic acid (0.10 mol) is combined with 2-arylpyrrolidine (0.10 mol) in xylenes (300 ml) and heated at reflux under a Dean-Stark trap for 45 hours. The solution is evaporated in vacuo to an oil, which is combined with PPA (20 g) and heated at 100° C. with occasional stirring for one hour. The mixture is poured into ice water (400 ml) and extracted with methylene chloride. The organic layer is washed with saturated NaCl, dried (MgSO$_4$), and evaporated in vacuo to give the crude lactam.

EXAMPLE C 1,2,3,10b-Tetrahydro-6-(4-methoxyphenyl)pyrrolo[2,1-a]isoquinoline-5(6H)-one (6)

4-Methoxymanpelic acid (26 g, 0.133 mol) was reacted with 2-phenylpyrrolidine (21 g, 0.143 mol) to give a brown oil, which was combined with PPA (300 g) and heated at 100° C. Work up furnished the desired lactams as a nearly 3:2 mixture of diastereomers (6a:6b) which were separated by HPLC.

General Procedure D.

The styrene oxide (0.10 mol) and 2-aryl-pyrrolidine (0.10 mol) are combined in absolute ethanol or tetramethylene sulfone (100 ml) and the solution is refluxed for 2 to 8 hours. For ethanol, the solution is evaporated in vacuo to an oil and, for sulfolane, it is diluted with a 5-fold volume of water. The oil is partitioned between ether and 1N HCl (1 liter). The aqueous solution is made alkaline with 50% NaOH and extracted with ether. The ether solution is dried (K$_2$CO$_3$) and evaporated in vacuo to an oil, which is combined with polyphosphoric acid (250 g), heated at 100° C. for 30 minutes and poured into 1 liter of crushed ice. The mixture is extracted with CH$_2$Cl$_2$ (4×500 ml portions). The organic layer is washed once with 50% NaOH, 3 times with water, dried (K$_2$CO$_3$), and evaporated in vacuo to give products.

EXAMPLE D 1,2,3,5,6,10bβ-Hexahydro-6α-[(3-trifluoromethyl)-phenyl]pyrrolo[2,1-a]isoquinoline (XLIX)

m-Trifluoromethylstyrene oxide (28.0 g, 80% assay, 0.12 mol) and 2-phenyl-pyrrolidine (19.9 g, 88% assay, 0.12 mol) were combined in absolute ethanol (120 ml) and treated according to the general procedure to give the crude product mixture (3/1 by GLC). The isomeric amines were separated by preparative HPLC (chloroform/ethyl acetate, 9:1) to give title compound XLIX, which was converted to its HCl salt.

EXAMPLE 2

Reduction of Lactams

General Procedure.

The intermediate lactams, e.g., III, IX and XIV, may be reduced to form the compounds of this invention by careful reduction with borane.THF. The lactam (0.018 mol) is dissolved in THF (40.0 mol) and added slowly to borane.THF (1.0M, 0.05 mol) at 0° C. The solution is heated at reflux for one hour and cooled to 0° C. Water (10.0 ml), followed by hydrochloric acid (12.0M, 15.0 ml), are added (both slowly). The reaction is stirred for two hours at ambient temperature. The THF is distilled off, 50 ml of water is added, and the solution is heated at reflux for 15 minutes. The solution is cooled in an ice bath, made alkaline with 1N NaOH, and extracted with methylene chloride. The organic phase is washed once with water, once with saturated NaCl, and dried (K$_2$CO$_3$). The solution is evaporated in vacuo to give the amine.

EXAMPLE

9-Chloro-6α-(4-chlorophenyl)-1,2,3,5,6,10bβ-hexahydropyrrolo[2,1-a]isoquinoline (XXXII)

Lactam 5b (6.0 g, 0.018 mol) and borane.THF (50.0 ml, 0.05 mol) were combined according to the general procedure. Work-up gave crude amine XXXII. The perchlorate salt was prepared from methylene chloride/2-propanol. Recrystallization from methanol afforded pure amine salt, XXXII.HClO$_4$, m.p. 242°–245° C.

EXAMPLE 3

Equilibration

Equilibration of Lactams

General Procedure.

The lactam (0.10 mol) is dissolved in 200 ml of DMSO. Water (20 ml) and K$_2$CO$_3$ (100 g) are added. The reaction is heated at reflux (generally using an oil bath at 130° C.) until equilibrium is reached. This usually required one to three hours of heating. Reaction progress is monitored by removing aliquots, quenching them in ice water, extracting with methylene chloride, and analyzing by GLC. The reaction is rapidly cooled with an ice bath and treated with water (500 ml) and methylene chloride (500 ml). The organic layer is separated, washed three times with water, once with saturated NaCl, and dried (MgSO$_4$). The solution is evaporated in vacuo to give a mixture of lactams, which is generally separated using liquid chromatography.

EXAMPLE 1,5,6,10bβ-Tetrahydro-6α-phenylpyrrolo[2,1-a]isoquinoline-3(2H)-one (IXb)

The crude mixture (93/7, GLC) of lactams IXa and IXb (19.5 g, 0.075 mol) was combined with 150 ml of DMSO, 15 ml of water and K$_2$CO$_3$ (7.5 g) according to the general procedure. At equilibrium the reaction was worked up to give a mixture (1/1, GLC) of lactams IXa and IXb (16.0 g, 82%). The lactams were separated using high performance liquid chromatography on a silica gel column. Lactam IXb was recrystallized from ethyl acetate to give white crystals, m.p. 126.5°–132.5° C.

Equilibration of Amines

General Procedure.

The amine (0.01 mol) is dissolved in 30 ml of DMSO and 30 ml of 10N NaOH (aqueous) and heated at reflux under N$_2$. When equilibrium is attained, the reaction is quickly cooled in an ice bath and treated with water (200 ml) and methylene chloride (300 ml). The organic phase is separated, washed three times with water, once with saturated NaCl, and dried (K$_2$CO$_3$). The solution is evaporated in vacuo to give a mixture of the amines.

EXAMPLE

9-Chloro-6α-(4-chlorophenyl)-1,2,3,5,6,10bβ-hexahydropyrrolo[2,1-a]isoquinoline (XXXII)

Compound XLII (0.50 g, 1.57 mmol) was dissolved in 5.0 ml of DMSO and 5.0 ml of 10N NaOH and heated at reflux under N$_2$. After one hour the reaction was worked up to give a mixture (2/1, GLC) of amines XLII and XXXII, which were separated by liquid chromatography. The perchlorate salt was obtained as in Example II.

EXAMPLE 4

1,2,3,5,6,10b-Hexahydro-6-phenylpyrrolo[2,1-a]isoquinoline-6-ol (XLIII)

A solution of 1,2,3,10b-tetrahydro-6-phenylpyrrolo[2,1-a]isoquinoline-5(6H)-one (XIV) (25.0 g, 0.095 mol) dissolved in 500 ml of dry THF under an atmosphere of $N_2$ was cooled to 5° C. Sodium hexamethyldisilazide (33.0 g, 0.18 mol) was added and the solution was vigorously stirred as dry $O_2$ was bubbled into the solution for 1.5 hours. The solution was evaporated in vacuo to an oil, which was partitioned between water (1.0 liter) containing sodium sulfite (50 g, 0.40 mol) and methylene chloride. The organic layer was washed one time with water, once with brine, dried over anyhydrous magnesium sulfate and evaporated in vacuo to give crude hydroxy lactams (26 g, 98%). These hydroxy lactams were separated using high performance liquid chromatography on silica gel columns. The lactam (3.9 g, 0.014 mol) in dry THF (75 ml) was added slowly to 1M $BH_3.THF$ (55 ml, 0.055 mol) with ice bath cooling. The solution was refluxed for 1 hour under $N_2$ and then cooled to 5° C. Methanol (50 mol) was slowly added and the solution was stirred at ambient temperature for 30 minutes and then evaporated in vacuo to yield an oily product. The hydrobromide salt was prepared in a mixture of methanol and 2-propanol, a white solid, mp 211°–212° C.

EXAMPLE 5

6-Fluoro-1,2,3,5,6,10b-hexahydro-6-phenylpyrrolo[2,1-a]isoquinoline

A solution of 1,2,3,5,6,10b-Hexahydro-6-hydroxy-6-phenylpyrrolo[2,1-a]isoquinolin-5-one (prepared as shown in the hydroxy lactam preparation of Example IV) (39.0 g, 0.14 mol) in dry methylene chloride (100 ml) was added dropwise over a period of 45 minutes to a cold (−78° C.) solution of diethylaminosulfotri-fluoride in dry methylene chloride (70 ml) under $N_2$. After stirring at −70° C. for 10 minutes, the solution was allowed to warm to room temperature over a period of 1 hour. The solution was cooled to 5° C. and water (200 ml) was added slowly. The organic layer was separated and washed one time with water, one time with brine, dried ($K_2CO_3$) and evaporated in vacuo to give a yellow solid (38 g, 97%). The isomeric fluoro amides were separated using high performance liquid chromatography on silica gel columns. The fluoro lactam (12.8 g, 0.045 mol) in dry THF (200 ml) was added slowly to 1M $BH_3.THF$ (190 ml, 0.19 mol) at 5° C. The solution was refluxed for 1 hour and then cooled to 5° C. Methanol (200 ml) was added slowly and stirred at ambient temperature for 2 hours. The solution was heated on a steam bath for 15 minutes and then evaporated in vacuo to an oil. This oil was partitioned between 1N hydrochloric acid (500 ml) and ether (200 ml). The aqueous solution was basified with 10% sodium hydroxide solution and extracted with methylene chloride. The organic solution was washed one time with water, one time with brine, dried ($K_2CO_3$) and evaporated in vacuo to yield an oily product (9.3 g, 77%). This was converted to its hydrochloride salt, a white solid, mp 192°–193° C. after recrystallization from 2-propanol.

For pharmaceutical purposes, the compounds according to the present invention are administered to warm-blooded animals enterally or parenterally as active ingredients in customary dosage unit form consisting essentially of an inert pharmaceutical carrier and one effective dosage unit (1–500 mg) of the active ingredient, such as tablets, coated pills, capsules, wafers, powders, solutions, suspensions, emulsions, syrups, suppositories, and the like. The daily human dosage range for the treatment of depression is about 10 to 2000 mg of a compound of the invention, e.g., 200 to 500 mg, for an average human. Of course, the exact dosage will vary according to the activity of the particular compound chosen and the weight and need of the patient. Such a dosage may be divided into 2–4 administrations per day.

The following examples illustrate a few pharmaceutical dosage unit compositions comprising a compound of the present invention as an active ingredient and represent suitable modes for putting the invention into practical use. The parts are parts by weight unless otherwise specified.

EXAMPLE 6

Tablets

The tablet composition is compounded from the following ingredients:

| | |
|---|---|
| 1,2,3,5,6,10bβ-Hexahydro-6α-phenylpyrrolo[2,1-a]isoquinoline (Xb) Fumarate | 100.0 parts |
| Lactose | 45.0 parts |
| Corn Starch | 45.0 parts |
| Colloidal silicic acid | 2.0 parts |
| Soluble starch | 5.0 parts |
| Magnesium stearate | 3.0 parts |
| TOTAL | 200.0 parts |

The active ingredient is admixed with part of the excipients, and the mixture is granulated with a solution of the soluble starch in water. After drying of the granulate, the remaining excipients are admixed with it, and the mixture is compressed into 100 mg tablets. Each tablet contains 50 mg of the pyrroloisoquinoline compound and is an oral dosage unit with effective pharmacologic action.

EXAMPLE 7

Coated Pills

The pill core composition is compounded from the following ingredients:

| | |
|---|---|
| 1,2,3,5,6,10bβ-Hexahydro-6α-phenylpyrrolo[2,1-a]isoquinoline (Xb) Fumarate | 100.0 parts |
| Lactose | 75.0 parts |
| Corn starch | 65.0 parts |
| Colloidal silicic acid | 2.0 parts |
| Soluble starch | 5.0 parts |
| Magnesium stearate | 3.0 parts |
| TOTAL | 250.0 parts |

The ingredients are compounded as described in Example 6, and the composition is compressed into 100 mg pill cores which are subsequently coated in a conventional manner with a thin shell consisting essentially of a mixture of sugar, talcum and gum arabic. Each coated pill contains 40 mg of the pyrroloisoquinoline compound and is an oral dosage unit composition with effective pharmacologic action.

EXAMPLE 8

Syrup

The syrup composition is compounded from the following ingredients:

| | |
|---|---|
| 1,2,3,5,6,10bβ-Hexahydro-6α-phenylpyrrolo[2,1-a]isoquinoline (Xb) Fumarate | 100.0 parts |
| Cane Sugar | 150.0 parts |
| Glycerol (twice distilled) | 250.0 parts |
| Methyl p-hydroxybenzoate | 3.0 parts |
| Propyl p-hydroxybenzoate | 2.0 parts |
| Flavorings, as desired | |
| Water (distilled) | 1,995.0 parts |
| TOTAL | 2,500.0 parts |

EXAMPLE 9

Tablets

The tablet composition is compounded from the following ingredients:

| | |
|---|---|
| 1,2,3,5,6,10bβ-Hexahydro-6α-(4-nitrophenyl)pyrrolo[2,1,a]-isoquinoline (XXXVIII) Hydrobromide | 100.0 parts |
| Lactose | 20.0 parts |
| Corn Starch | 20.0 parts |
| Colloidal silicic acid | 2.0 parts |
| Soluble Starch | 5.0 parts |
| Magnesium stearate | 3.0 parts |
| TOTAL | 150.0 parts |

The active ingredient is admixed with part of the excipients, and the mixture is granulated with a solution of the soluble starch in water. After drying of the granulate, the remaining excipients are admixed with it, and the mixture is compressed into 100 mg tablets. Each tablet contains 50 mg of the pyrroloisoquinoline compound and is an oral dosage unit with effective pharmacologic action.

EXAMPLE 10

Coated Pills

The pill core composition is compounded from the following ingredients:

| | |
|---|---|
| 4-(1,2,3,5,6,10bβ-Hexahydro-pyrrolo[2,1-a]isoquinolin-6α-yl)benzenamine (XLVIII) Hydrobromide | 100.0 parts |
| Lactose | 45.0 parts |
| Corn Starch | 45.0 parts |
| Colloidal silicic acid | 2.0 parts |
| Soluble starch | 5.0 parts |
| Magnesium stearate | 3.0 parts |
| TOTAL | 200.0 parts |

The ingredients are compounded as described in Example V, and the composition is compressed into 150 mg pill cores which are subsequently coated in a conventional manner with a thin shell consisting essentially of a mixture of sugar, talcum and gum arabic. Each coated pill contains 75 mg of the pyrroloisoquinoline compound and is an oral dosage unit composition with effective pharmacologic action.

EXAMPLE 11

[6α,10bα]-6-(4-aminophenyl)-1,2,3,5,6,10b-hexahydropyrrolo[2,1-a]-isoquinoline 24.2 g of the nitro compound 1,2,3,5,6,10bα-hexahydro-6α-(4-nitrophenyl)pyrrolo[2,1-a]isoquinoline (LIV) in 600 ml of ethanol is treated with 2.5 g of PtO$_2$ and warmed to dissolve the substrate, if necessary. The mixture is hydrogenated at 45 psig for about 45 minutes. Filter aid (3 g) is added and the reaction is filtered. The solution is evaporated to a light tan syrup, which eventually crystallizes on prolonged standing. The monohydrobromide salt, prepared in 2-propanol with 48% HBr, is recrystallized from methanol to give light tan leaflets, mp 252°–258° C.

EXAMPLE 12

[6α,10bα]-6-(4-acetylaminophenyl)-1,2,3,5,6,10b-hexahydropyrrolo[2,1-a]-isoquinoline To 2.0 g of the aniline product of Example 11 in 15 ml of dry CH$_2$Cl$_2$ was slowly added 650 mg of acetylchloride in 5 ml of CH$_2$Cl$_2$, with stirring. After 16 hours, the acetylchloride reaction was basified with 1N aqueous NaOH and the organic layer was separated. The aqueous layer was extracted and the combined CH$_2$Cl$_2$ solution was dried (Na$_2$SO$_4$) and concentrated to a tan solid. Recrystallization from ethyl acetate gave tan leaflets, mp 175°–178° C.

EXAMPLE 13

[6α,10bα]-6-(4-benzoylaminophenyl)-1,2,3,5,6,10b-hexahydropyrrolo[2,1-a]isoquinoline To 2.0 g of the aniline product of Example 11 in 15 ml of dry CH$_2$Cl$_2$ was added slowly 1.10 g of benzoylchloride in a 5 ml of CH$_2$Cl$_2$ with stirring. After 16 hours, the benzoylchloride reaction was diluted with dry ether, cooled to 0° C., and filtered to give a gray solid. The solid was recrystallized from methanol to give a white powder, mp 261°–274° C.

EXAMPLE 14

[6α,10bα]-6-(4-ethylamino)-1,2,3,5,6,10b-hexahydropyrrolo[2,1-a]isoquinoline

To 2.6 g of the amide produced in Example 12 in 20 ml of dry THF was slowly added 30 ml of 1M BH$_3$—THF at 5° C. under an inert atmosphere. The reaction was refluxed for 1 hour, cooled in ice and treated with 6 ml of H$_2$O and then 9 ml of 12N HCl. The THF was distilled off and the reaction refluxed an additional 10 minutes. The solution was ice bath cooled and 3N NaOH was added until the pH was greater than 11 and then extracted with methylene chloride. The organic layer was dried (K$_2$CO$_3$) and evaporated in vacuo to an oil. The fumarate salt was prepared from methanol/2-propanol to give white crystalline material (1.95 g), mp 170°–172° C.

EXAMPLE 15

[6α,10bβ]-6-(4-cyanophenyl)-1,2,3,5,6,10b-hexahydropyrrolo[2,1-a]isoquinoline 35.2 g (0.107 mole) of the bromide, a mixture of [6α,10bα]- and [6α,10bβ]-6-(4-bromophenyl)-1,2,3,5,6,10b-hexahydropyrrolo[2,1-a]isoquinoline produced via the styrene-oxide route (D), 19.21 g (0.215 mole) of cuprous cyanide and 1.0 g of tetrakistriphenylphosphine palladium (O) were combined in 10$^7$ ml of N,N-dimethylacetamide under an inert atmosphere. The reaction was refluxed for 18 hours, cooled and partitioned between 1 liter of conc. ammonium hydroxide and 250 ml of ether. The aqueous layer was extracted several times with ether and the combined ether solution was washed 2 times with ammonium hydroxide, 2 times with water, 3 times with brine, dried ($K_2CO_3$) and evaporated in vacuo to an oily product (22.6 g, 77%). The α and β isomers were separated by preparative HPLC and the 10bβ isomer was isolated. The 10bβ HCl salt was recrystallized from methanol to give an off-white soldi, mp 271°–276° C.

EXAMPLE 16

[6α,10bβ]-6-(4-carboxamidophenyl)-1,2,3,5,6,10b-hexahydropyrrolo[2,1-a]isoquinoline 200 mg of the oily cyano compound produced in Example 15 as the 10bα and 10bβ isomer mixture was combined with 150 mg of KOH in 1 ml of t-butanol and refluxed for 30 minutes. The cooled solution was extracted between methylene chloride and saturated NaCl. The organic layer was dried ($K_2CO_3$) and evaporated in vacuo to a glassy material. The glassy material was then subjected to preparative HPLC to separate the α and β isomers whereby the 10bβ isomer was isolated.

What is claimed is:

1. A compound of the following formula I including diastereomers and the nontoxic, pharmaceutically-acceptable acid addition salts thereof,

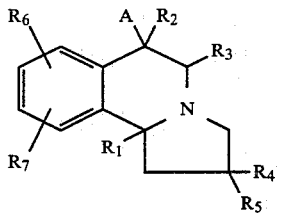

wherein
said compound has 6α,10bβ stereochemistry with respect to the A and $R_1$ moieties, respectively;
$R_1$ is hydrogen or lower alkyl having one to four carbons;
$R_2$ is hydrogen, lower alkyl having one to four carbons, fluoro, hydroxy, or lower alkoxy having one to four carbons;
$R_3$ is hydrogen, methyl, or phenyl;
$R_4$ and $R_5$ are the same and both are hydrogen, or are different and each is selected from the group of hydrogen or lower alkyl having one to four carbons;
$R_6$ and $R_7$ are the same or different and each is selected from the group hydrogen, lower alkyl having one to four carbons, lower alkoxy having one to four carbons, hydroxy, or halogen, or else are taken together as methylenedioxy; and
A is selected from the group of units of the following formulas (1) or (3):

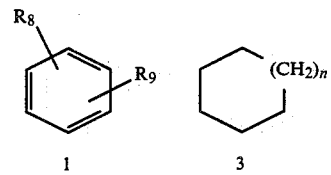

wherein for the benzene unit of formula (1), $R_8$ and $R_9$ are selected from the group hydrogen, lower alkyl having one to six carbons, perfluoro(lower-)alkyl having one to four carbons, hydroxy, lower alkoxy having one to four carbons, carb(lower)alkoxy having one to five carbons, lower alkanoylamino (one to five carbons), benzoylamino, cyano, carboxamido, lower alkanoyl of one to five carbons, lower alkylthio having one to four carbons, lower alkylsulfonyl having one to four carbons, nitro, amino, loweralkyl or di(lower)alkylamino having one to four carbons in each alkyl, or halogen; and wherein for the cycloalkyl unit of formula (3), n=0 to 2, which units of formulas (1) and (3) may be attached at any carbon atom vertex.

2. A compound according to claim 1 wherein in formula (I), $R_3$, $R_4$, and $R_5$ are all hydrogen.

3. A compound according to claim 1, wherein in formula (I), $R_2$, $R_3$, $R_4$, $R_5$, $R_6$ and $R_7$ are hydrogen and A is a unit of formula 1.

4. A compound according to claim 1 which is the free base or acid addition salt form of:
[6α,10bβ]-1,2,3,5,6,10b-hexahydro-10b-methyl-6-phenylpyrrolo[2,1-a]isoquinoline;
[6α,10bβ]-1,2,3,5,6,10b-hexahydro-6-phenylpyrrolo[2,1-a]isoquinoline;
1,2,3,5,6,10bβ-hexahydro-6-methyl-6α-phenylpyrrolo[2,1-a]isoquinoline;
[6α,10bβ]-1,2,3,5,6,10b-hexahydro-8,9-dihydroxy-6-phenylpyrrolo[2,1-a]isoquinoline;
[6α,10β]-6-cyclohexyl-1,2,3,5,6,10b-hexahydropyrrolo[2,1-a]isoquinoline;
[6α,10bβ]-6-(4-chlorophenyl)-1,2,3,5,6,10b-hexahydropyrrolo[2,1-a]isoquinoline;
1,2,3,5,6,10bβ-hexahydro-6α-(4-methoxyphenyl)pyrrolo[2,1-a]isoquinoline;
1,2,3,5,6,10b-hexahydro-6-phenylpyrrolo[2,1-a]isoquinolin-6-ol;
4-(1,2,3,5,6,10bβ-hexahydropyrrolo[2,1-a]isoquinolin-6α-yl)benzene-1,2-diol;
1,2,3,5,6,10bβ-hexahydro-6α-(4-nitrophenyl)pyrrolo[2,1-a]isoquinoline;
1,2,3,5,6,10bβ-hexahydro-6α-(3-methoxyphenyl)pyrrolo[2,1-a]isoquinoline;
3-(1,2,3,5,6,10bβ-hexahydropyrrolo[2,1-a]isoquinolin-6α-yl)phenol;
1,2,3,5,6,10bβ-hexahydro-6α-(3,4-dimethoxyphenyl)-pyrrolo[2,1-a]isoquinoline;
1,2,3,5,6,10bβ-hexahydro-7-methoxy-6α-phenylpyrrolo[2,1-a]-isoquinoline;
1,2,3,5,6,10bβ-hexahydro-6α-[(3-trifluoromethyl)-phenyl]pyrrolo[2,1-a]isoquinoline;
9-fluoro-6α-(4-fluorophenyl)-1,2,3,5,6,10b-hexahydro-10bβ-methylpyrrolo[2,1-a]isoquinoline;
[6α,10bβ]-6-(2-chlorophenyl)-1,2,3,5,6,10b-hexahydropyrrolo[2,1-a]isoquinoline; or
1,2,3,5,6,10bβ-hexahydro-6α-(4-methylthiophenyl)pyrrolo[2,1-a]iosquinoline.

5. A compound of claim 1, which is the free base or acid addition salt of 1,2,3,5,6,10bβ-hexahydro-6α-[(3-trifluoromethyl)phenyl]pyrrolo[2,1-a]isoquinoline.

6. A compound of claim 1, which is the free base or acid addition salt of [6α,10bβ]-6-(2-chlorophenyl)-1,2,3,5,6,10b-hexahydropyrrolo[2,1-a]isoquinoline.

7. A compound of claim 1, which is the free base or acid addition salt of 1,2,3,5,6,10bβ-hexahydro-6α-(4-methyl thiophenyl)pyrrolo[2,1-a]isoquinoline.

8. A compound of claim 1, wherein A is a unit of Formula (1).

9. A psychotropic pharmaceutical composition comprising a psychotropically effective amount of a compound of claim 1 in combination with a pharmaceutically acceptable diluent or carrier.

10. A method of treating depression in a mammal which comprises administering to the mammal an antidepressant amount of the pharmaceutical composition of claim 9.

11. A compound of claim 1, wherein for the benzene unit of formula (1), $R_8$ and $R_9$ are selected from the group hydrogen, lower alkyl having one to six carbons, perfluoro(lower)alkyl having one to four carbons, hydroxy, lower alkoxy having one to four carbons, carb-(lower)alkoxy having one to five carbons, lower alkanoylamino (one to five carbons), lower alkanoyl of one to five carbons, lower alkylthio having one to four carbons, lower alkylsulfonyl having one to four carbons, nitro, amino, loweralkyl- or di(lower)alkyl-amino having one to four carbons, or halogen.

12. A compound according to claim 3 wherein $R_8$ is hydrogen.

* * * * *